the layers, the aqueous layer was extracted with a second portion of EtOAc. The combined organics were washed with H₂O and brine, then dried (MgSO₄) and stripped of solvent to give a semisolid gum. Trituration with Et₂O left a white solid undissolved which was removed by filtration (imidazolide). The filtrate was stripped of solvent, redissolved in 6 ml of 1:1 Et₂O-CHCl₃ and filtered through a 3" layer of basic alumina in a sintered glass funnel, eluting with 400 ml of 1:1 Et₂O-CHCl₃ + 2% MeOH solution. Stripping of the filtrate gave purified 5-endo(indole-3-carbonyloxy)-N-(N'-benzyloxycarbonyl-3-isopropylaminopropyl)bicyclo[2.2.1]heptane-2,3-di-endo-carboxylic acid imide as an oil (0.585 g). Hydrogenolysis of this intermediate was carried out in a Parr shaker at 48 psi in 100 ml of absolute EtOH, using 0.4 g of 30% Palladium on Celite as catalyst. The H₂ uptake was 7.5 lbs. over 1.25 hr. Removal of the catalyst and solvent afforded a white froth (0.448 g) which was redissolved in 1:1 abs EtOH-Et₂O and treated with HCl gas. Solvent removal and treatment of the residue with boiling 10:1 EtOAc-EtOH gave Io as a white solid (0.219 g). Initial elemental analysis indicated that the material had coordinated with a metal at some stage. It was, therefore, slurried in EtOAc and converted back to the free base by treatment with 3% Na₂CO₃ solution. The organic layer was then washed with 3 portions of H₂O, dried over Na₂SO₄ and stripped. Formation of the .HCl salt in abs EtOH-EtOAc in the usual manner gave Io as a white solid (0.188 g). Recrystallization from abs. EtOH afforded analytical material; mp 274°–275° (d).

Anal. calc'd. for $C_{24}H_{29}N_3O_4 \cdot HCl$: C, 62.67; H, 6.57; N, 9.14.

Found: C, 62.79; H, 6.46; N, 9.13.

We claim:

1. A compound having the formula

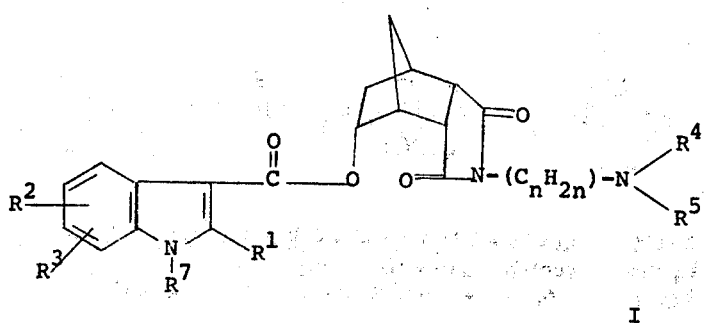

wherein $R^1$ is H, Cl, Br, F or (lower)alkyl, $R^7$ is H or methyl, $R^2$ and $R^3$ are alike or different and each is H, Cl, Br, F, (lower)alkyl, nitro, $CF_3$, OH or (lower)alkoxy, n is an integer of 2 to 4 inclusive and $R^4$ and $R^5$ are alike or different and each is H, (lower)alkyl or when taken together with the nitrogen a radical of the formula

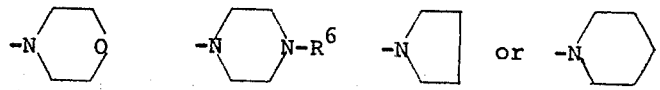

in which $R^6$ is (lower)alkyl; or a pharmaceutically acceptable acid addition salt thereof.

2. A compound having the formula

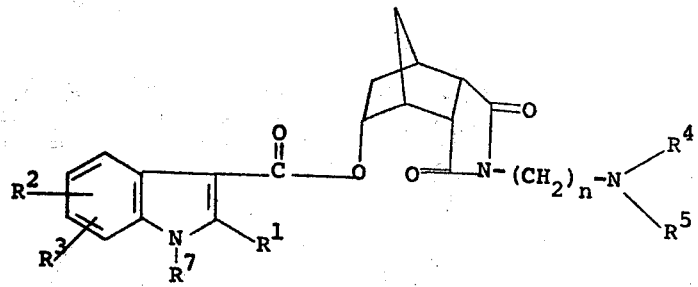

wherein $R^1$ is H, Cl, Br, F or (lower)alkyl, $R^7$ is H or methyl, $R^2$ and $R^3$ are alike or different and each is H, Cl, Br, F, (lower)alkyl, nitro, $CF_3$, OH or (lower)alkoxy, n is an integer of 2 to 4 inclusive and $R^4$ and $R^5$ are alike or different and each is H, (lower)alkyl or when taken together with the nitrogen a radical of the formula

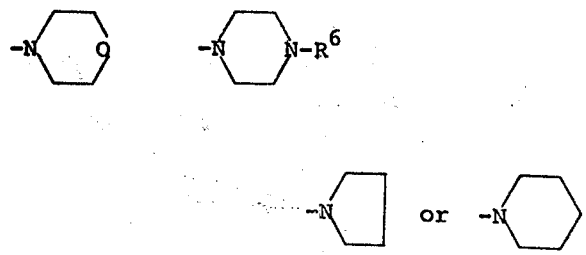

in which $R^6$ is (lower)alkyl; or a pharmaceutically acceptable acid addition salt thereof.

3. A compound of claim 2 having the formula

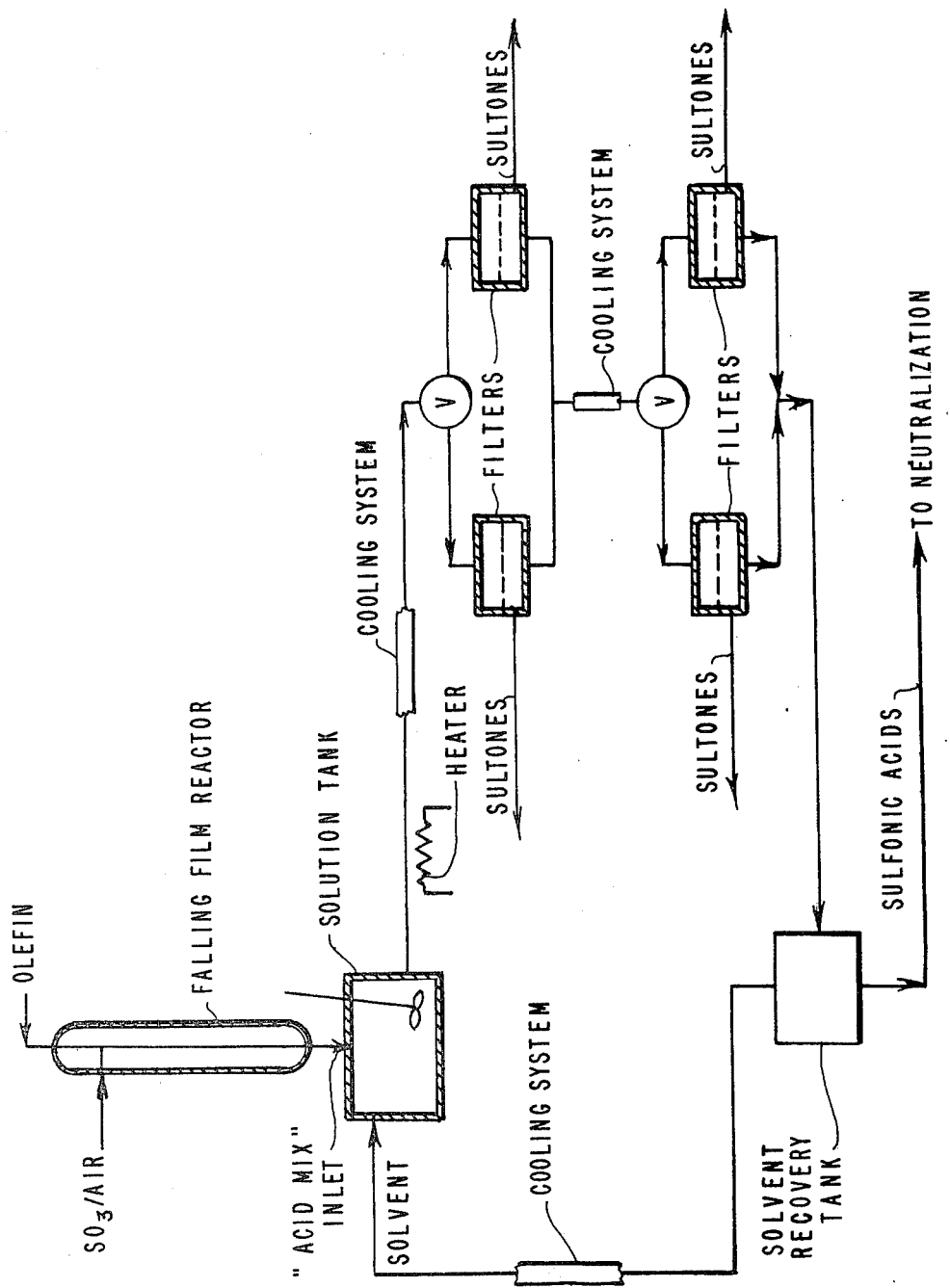

CONTINUOUS PROCESS FOR MANUFACTURING GAMMA SULTONES

RELATED APPLICATIONS

This is a continuation of application Ser. No. 224,924 filed Feb. 9, 1972, now abandoned, which application is a continuation-in-part of application Ser. No. 848,457 filed Aug. 8, 1969, now abandoned.

The invention relates to a novel process for the continuous production of gamma sultones.

Sultones, particularly gamma sultones having the structure

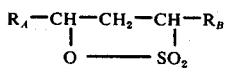

where $R_A$ is a monovalent hydrocarbon radical having 2 to 27 carbon atoms, and $R_B$ is hydrogen or a monovalent hydrocarbon radical having 1 to 27 carbon atoms, and the maximum number of carbon atoms is 30, are very important intermediates in the synthesis of surfactants. However, when sultones are conventionally produced by sulfonating olefins with $SO_3$, the sulfonation product is a very complex "acid mix," containing not only gamma and delta sultones, but unsaturated sulfonic acids, disulfonic acids, etc. Since the gamma sultones are the most useful detergent intermediates in the "acid mix," it is desirable to separate these gamma sultones from the "acid mix" so that they may be reacted further to produce superior detergents. Thus the process of this invention is highly desirable since it produces gamma sultones directly from an "acid mix," thereby eliminating the need for separating the sulfonic acids from the solution before crystallizing the gamma sultones.

Thus, it is an object of this invention to produce gamma sultones by a continuous process.

Another object is to produce gamma sultones directly from the "acid mix" obtained when olefins are reacted with $SO_3$.

A further object is to produce gamma sultones in high yield.

A still further object is to produce gamma sultones which are free from contamination.

These objects are realized when gamma sultones are produced by the following process:

1. Olefins are reacted with at least equimolar amounts of $SO_3$ to produce an "acid mix."
2. The "acid mix" is dissolved in a low boiling organic solvent.
3. The solvent-"acid mix" solution is cooled so that the gamma sultones crystallize.
4. The gamma sultone crystals are collected.
5. The solvent is recovered from the solution.
6. The "acid mix" residue is neutralized and hydrolyzed.

The FIGURE is a flow diagram of a preferred aspect of a continuous process of this invention.

The olefin feedstock used in the reaction with $SO_3$ may contain olefins of the formula $R-CH=CH-R_1$, where R is an alkyl radical and $R_1$ is an alkyl radical or hydrogen, preferably hydrogen. The olefins should contain a total of 5 to 30 carbon atoms, preferably 12 to 21 carbon atoms.

Mixtures which contain alkenes of various molecular weights, such as mixtures containing straight chain primary alkenes may be used. Examples of satisfactory alkenes for use in the solfonation process are amylene, hexene, nonene, dodecene, tetradecene, hexadecene, heptadecene, octadecene, docosene, pentacosene and the like, as well as mixtures of said alkenes.

A preferred alkene for use in the present invention is an alkene or olefin having a terminal double bond and an essentially acyclic straight-chain structure which contains about 8 to 25 carbon atoms in the molecule. These alpha-olefins or 1-alkenes may consist essentially of a single compound or mixtures of said compounds, although the olefin feed also may contain secondary or internal olefins, diolefins, cyclic olefins, aromatics, naphthenes, and alkanes. Monoolefins having the structure $R-CH=CH-R_1$ (where R and $R_1$ have the meaning previously given) preferably constitute at least ¾, still more preferably more than ⅞, and even more preferably more than 9/10 of the feedstock. Best results have thus far been obtained when alphaolefins (where $R_1$ is H) constitute a major proportion, for example above 70 percent and preferably at least 90 percent, of the feedstock. It is within the scope of the invention, however, to use internal olefins, such as, hexadecene-2, tetradecene-3, or a mixture made by isomerizing the olefin to redistribute its double bond (as by isomerization treatment with concentrated $H_2SO_4$ or other isomerization catalyst). The olefin may be present in a cut containing, for instance, olefins having 11 to 14 carbon atoms, 15 to 18 carbon atoms, or 12 to 21 carbon atoms.

Generally, the alkene or olefin feed materials may be derived from primary, secondary, and tertiary alcohols by dehydration, from halogenated hydrocarbons by dehalogenation, from saturated hydrocarbons through cracking or catalytic dehydrogenation, or by polymerization of olefins such as ethylene, butylene, propylene and the like. Particularly satisfactory materials may be obtained by cracking petroleum wax or catalytic polymerization of ethylene. The alkene can also be produced by dehydration of long chain fatty alcohols.

In the sulfonation reaction the inert gas: $SO_3$ mole (volume) ratio is generally in the range of 5:1 to 50:1, preferably at least about 10:1, such as 50:1 to 20:1. The $SO_3$ gas may be used in two or more stages at different $SO_3$ concentrations and/or pressures. In accordance with a specific aspect of the invention, the amount of $SO_3$ reactant should be in the range of from 1.0 to 1.5 moles of $SO_3$ for each mole of olefin reacted. This mole ratio of $SO_3$ to olefin results in a reaction product containing virtually no olefin starting material and a very high sultone and very low sulfonic acid content.

Among the inert gases which may be used for dilution of the $SO_3$ are air and nitrogen, which are preferred, carbon dioxide, sulfur dioxide, etc. The gaseous $SO_3$ may be provided by vaporizing a stabilized liquid $SO_3$ or by using converter gas obtained from a sulfur burner.

In carrying out the initial $SO_3$-olefin reaction, it is advantageous to maintain intimate contact between a supply of gaseous $SO_3$ and the olefin. This may be conveniently effected in a continuous manner by exposing the $SO_3$ to either one or both faces of a thin flowing film of olefin, as by passing the thin film of olefin down the wall of a tube into the inner portion of which the $SO_3$ is injected.

During the initial SO₃-olefin reaction the temperature is advantageously maintained below 80°C.; a temperature of less than about 70°C. and, when feasible, not above about 60°C is preferred. In general, it is desirable to use as low a temperature as possible; for example, a temperature which is 5°C., or less, above the temperature at which freezing or precipitation takes place. In accordance with a further specific aspect of the invention, the SO₃-olefin reaction takes place between 10°C. and 70°C. at which temperatures the reaction product is in a liquid state. Since the reaction between the SO₃ and the olefin is exothermic, it is advantageous to use suitable cooling medium, such as water, through a jacket surrounding the tubular reactor in which the SO₃-olefin reaction is taking place.

The solvent used in this process is an organic solvent. Water-immiscible solvents such as hydrocarbons having 4 to 8 carbon atoms and halohydrocarbons having 1 to 8 carbon atoms and 1 to 8 halogen atoms may be used (for example, pentane, hexane; carbontetrachloride, methylene chloride, and "Freons" such as dichlorodifluoromethane, 1-chloro-1,1-difluoroethane, etc.) Water-miscible solvents such as lower alcohols having 1 to 4 carbon atoms and lower ketones having 3 to 4 carbon atoms such as methanol, ethanol, or isopropanol and acetone or methyl ethyl ketone may be used. The preferred solvents are low boiling saturated hydrocarbon petroleum fractions having a 4 to 8 carbon atom chain. Pentane and hexane are particularly preferred.

In accordance with a further specific aspect of the invention, at least one part solvent per part acid mix should be used in diluting the reaction mixture. Preferably the ratio of solvent to reaction mixture should be between 1:1 and 5:1, most preferably, about 3:1. The solvent should be at a temperature in the range of 15°C to 50°C. or higher, most preferably between 20°C. and 40°C.

After the solvent is added to the reaction mixture, the temperature of the mix is adjusted, if necessary, to a value between 15°C and 35°C. The solvent-acid mix solution is then cooled to below 10°C., preferably between 0°C. and 5°C., using any conventional methods such as an ice water bath, cooling coil, heat exchange, etc. Upon cooling, the gamma sultone component precipitate as fine crystals.

After the precipitation of the gamma sultones, the precipitate may be separated easily from the solution by filtration, centrifugation, or decantation. The separation means is preferably a filter and more preferably a pair of filters placed in parallel. It is desirable to have the filters in parallel so that one filter may be emptied of gamma sultone crystals while the other filter is collecting crystals. Thus the whole process can be operated without interruption. Several such pairs of parallel filters may be placed, if desired, in series in the system.

The filtrate containing the unsaturated sulfonic acids and delta sultones is passed through an evaporator (for example, falling film evaporator) where the solvent is recovered and recycled. A suitable temperature for the solvent evaporation is less than 50°C. (from 0° to 50°C.). A temperature of about 40°C. is desirable when the solvent is hexane. A cooling coil may be used to effect the condensation of the solvent if necessary.

The remaining "acid mix" residue is unsaturated sulfonic acids and delta sultones which are then hydrolyzed and neutralized by methods known in the art. The neutralizing base may be added dry (as a powder) or preferbly as a relatively concentrated aqueous solution. Excellent results have been obtained by the use of sodium hydroxide added, for example, in the form of a 50-percent aqueous solution. (A 10-percent sodium hydroxide solution is often used.) A solution of sodium methoxide in ethanol has also been employed. Other bases which may be added are other sodium alcoholates (for example, sodium ethoxide) and basic salts such as the carbonates. The temperature during treatment with the base may be in the range of about 15° to 20° to 50°C. or higher. The amount of base is generally at least about equal to the amount stoichiometrically equivalent to the acid content of the reaction mixture. It is often convenient to use some excess base (for example, 20-percent excess) to ensure complete neutralization; a very large excess is less desirable since the base, together with the water carried with the base, can be occluded onto the precipitated salt. The base need not be one which yields a sodium salt; for example, bases, such as potassium hydroxide or lithium hydroxide, which yield other alkali metal salts or those which yield ammonium salts may be used.

Reference to the flow diagram of the FIGURE will clarify a preferred continuous procedure by which the process of this invention can be carried out according to the conditions described above. Olefins and SO₃ are reacted in a reactor. The resulting "acid mix" flows via an "acid mix" inlet into the solution tank where said "acid mix" is combined using agitation with a solvent. The "acid mix"-solvent solution is passed through a cooling system, and the crystallized gamma sultones are collected by filtration. The filtrate goes to the solvent recovery system where the solvent is recovered for recyling. The remaining unsaturated sulfonic acids and delta sultones are then hydrolyzed and neutralized.

The principal features and inventive nature of this process having thus been presented, the following examples serve to illustrate some of its applications. However, these examples should not be considered to be limiting in any sense.

EXAMPLE I

Hexadecene (0.70 gram/min) and sulfur trioxide (0.28 gram/min), (1:1 mole ratio) are reacted continuously on a falling film reactor. The "acid mix" thus produced contains about 20-percent gamma sultone (determined by means of infrared spectroscopy on a petrol ether extract of "acid mix" that had been cautiously neutralized in the cold).

As it is produced, the "acid mix" is continually mixed with hexane (3.0 ml/min), and the mixture is continually transported to a flask where it is heated to about 25°C., so that a clear solution is obtained. The clear solution is then continually transported into a second flask, which is cooled in an ice bath to about 5°C., thereby precipitating the gamma sultone from the solution. The resulting slurry is then continually transported into a third flask, where it is cooled further to ensure complete precipitation of the gamma sultone. The slurry is then continually passed through a filter system, which consists of a Buchner funnel and a suction flask, which separate the gamma sultone from the mother liquor.

After 90 minutes the process is interrupted, the crude gamma sultone is washed with cold hexane and dried. Yield: 13.5 grams (80 percent based on available gamma sultones).

The transportation of the "acid mix"-hexane solution is effected by applying a slight vacuum to the filtering flask, thereby creating a pressure gradient throughout the system. Any suitable pumping system may be used to effect the transfer of solution throughout the system.

EXAMPLES II – IV

In these examples the process of Example I is followed except that methylene chloride, isopropanol, and methyl ethyl ketone are each used as the solvent medium. In all runs the results and yields are approximately the same as those of Example I.

Thus it is seen that the process of this invention produces gamma sultones in high yield, and moreover, the product is free from contamination.

The gamma sultone intermediates which are the desired product of the instant continuous process are used to produce novel compounds having unique overall characteristics and properties which make them particularly suitable in the formulation of detergent compositions. Among these characteristics are outstanding detergency properties which make the products highly suitable for washing clothes in hot or cold and hard or soft water. The compounds impart to the fabrics being washed an unexpected and highly desirable softness, often making it unnecessary to use a separate fabric softener. Moreover, the novel products also have significant bactericidal properties.

The novel compounds produced from the gamma sultone intermediates have the following formula:

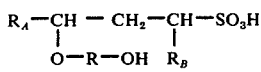

wherein $R_A$ is a monovalent hydrocarbon having 2 to 27 carbon atoms, $R_B$ is hydrogen or a monovalent hydrocarbon having 1 to 27 carbon atoms, O-R-OH is the radical of a polyhydric alcohol of the formula HO-R-OH, where R is a hydrocarbon having 2 to 20 carbon atoms, preferably 2 to 15 carbon atoms, and more preferably 2 to 10 carbon atoms, and the maximum number of carbon atoms is 30.

The compounds are prepared by reacting a gamma sultone of the formula:

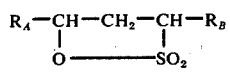

with a polyhydric alcohol of the formula HO-R-OH. (R, $R_A$, and $R_B$ are as defined above).

The proportions of polyhydric alcohol and sultone may be varied. To convert gamma sultones in high yield to the desired hydroxy ether sulfonates it is desirable to employ at least about 1 mole of polyhydric alcohol per mole of gamma sultone. Larger amounts, for example, 2, 3, 4, or 5 moles of polyhydric alcohol per mole of gamma sultone may also be employed, and the excess unreacted glycol or other polyhydric alcohol may, if desired, be removed from the reaction mixture (as by vacuum distillation).

Among the polyhydric alcohols which may be employed are the glycols such as ethylene glycol, 1,2- or 1,3-propanediol, 1,4- or 1,3-butanediol, 1,6-hexanediol, 1,8-octanediol, 1,10-decanediol, 1,2- or 1,12-dodecanediol, etc. Ether glycols such as diethylene glycol, triethylene glycol, etc. may be used. Trihydric alcohols (such as glycerol) have given good results, and other alcohols having three or more hydroxyl groups such as hexanetriol-1,2,4 or pentaerythritol may be used. Alicyclic, heterocyclic, or aromatic polyhydric alcohols may be used, for example, 1,4-cyclohexanediol, dihydroxyethylthiophene, or dihydroxyethylbenzene. The alcohol may contain olefinic unsaturation, for example, 1,6-dihydroxyhexene-3.

Generally, alcohols having less than about 20 carbon atoms and less than 4 hydroxyl groups are preferred. Especially good results have been obtained with relatively short chain glycols such as ethylene glycol and diethylene glycol. Mixtures of two or more different polyhydric alcohols may be used, such as a mixture of equal parts of ethylene glycol and glycerol or of diethylene glycol and triethylene glycol.

The products may be used, for detergent purposes, in the form of their sodium salts. The compounds may also be converted to other salts, using other cations in place of all or part of the sodium, for example, potassium lithium, calcium, magnesium, zinc, aluminum, lead, chromium, ammonium, triethanolammonium, diethanolammonium, monoethanolammonium, tri-, di-, or monopropanolammonium, hydrazinium, trimethyl- or triethylammonium, etc.

The hydroxy ether sulfonates can be produced by adding the polyhydroxy alcohol directly to the "acid mix." However, since the gamma sultones constitute only 20 percent of the "acid mix", only 20 percent of the "acid mix" is converted to the desired hydroxy ether sulfonates. Therefore, the process of this invention which separates gamma sultones from an "acid mix" is highly desirable. Specific details on the preparation of hydroxy ether sulfonates and on the formulation of these compounds are found in U.S. Pat. application No. 736,753 filed June 13, 1968, now abandoned.

The new hydroxy ether sulfonate compounds may be employed for a wide variety of uses based, for instance, on their foaming, wetting, penetrating, emulsifying, dispersing, and solubilizing properties. Thus they may be used in detergent compositions, including light-duty liquid detergent formulations and granular compositions such as spray-dried built detergent powders, scouring powders, and spot-cleaning or dry-cleaning compositions. They may be used in toilet bars for washing the hands, face, and body (here, as in other formulations, their unexpected germicidal properties are highly advantageous) or in laundry detergent bars, containing appreciable amounts of builder salts, for washing clothes. They may also be used in hair-shampooing, hair-dyeing, half-waving, or other hair-treating or hair-conditioning compositions. They may also be used in dental creams or other dentifrices and in skin care preparations such as lotions or creams, for example cold creams, vanishing creams, absorption base creams, deodorants, make-up and facial preparations, shaving creams or other shaving preparations, bath preparations, etc. They may be used in metal cleaning formulations, rust and corrosion inhibiting compositions, electroplating baths, photographic developing baths, cutting oils, leather degreasing and fat-liquoring compositions, assistants in textile treating baths, petroleum based lubricating oils or greases, or lubricating detergents (for example, in the form of their polyvalent metal salts).

The novel hydroxy ether sulfonate compounds may be used as such or in combination with other surface-active detergents. The added surface-active detergents may be of the anionic, nonionic, cationic, or amphoteric types, or mixtures thereof.

The anionic surface active agents which may be used with the novel hydroxy ether sulfonate compounds include those surface active or detergent compounds which contain an organic hydrophobic group and an anionic solubilizing group. Typical examples of anionic solubilizing groups are sulfonate, sulfate, carboxylate, phosphonate, and phosphate. Examples of suitable anionic detergents which fall within the scope of the invention include the soaps, such as the water-soluble salts of higher fatty acids or resin acids, such as may be derived from fats, oils, and waxes of animal, vegetable, or marine origin, for example sodium soaps of tallow, grease, coconut oil, tall oil, and mixtures thereof; and the sulfated and sulfonated synthetic detergents, particularly those having about 8 to 26, and preferably about 12 to 22, carbon atoms to the molecule.

Examples of suitable synthetic anionic detergents are the higher alkyl mononuclear aromatic sulfonates such as the higher alkyl benzene sulfonates containing from 10 to 16 carbon atoms in the straight or branched-chain alkyl group, for example, the sodium salts of higher alkyl benzene sulfonates or of the higher alkyl toluene, xylene, and phenol sulfonates; alkyl naphthalene sulfonate, ammonium diamyl naphthalene sulfonate, and sodium dinonyl naphthalene sulfonate. In one preferred type of composition a linear alkyl benzene sulfonate is used which has a high content of 3- (or higher) phenyl isomers and a correspondingly low content (well below 50 percent) of 2- (or lower) phenyl isomers; in other terminology, the benzene ring is preferably attached in large part at the 3 or higher (for example 4, 5, 6, or 7) position of the alkyl group and the content of isomers in which the benzene ring is attached at the 2 or 1 position is correspondingly low. Particularly preferred materials are set forth in U.S. Pat. No. 3,320,174 issued on May 16, 1967 to J. Rubinfeld.

Mixtures containing linear alkylbenzene sulfonates and the novel hydroxy ether sulfonate compounds have unexpectedly good detergent properties and particularly good softening power.

Other anionic detergents are the olefin sulfonates, including long chain alkene sulfonates, long chain hydroxyalkane sulfonates or mixtures of alkenesulfonates and hydroxyalkanesulfonates. These olefin sulfonate detergents may be prepared in known manner and are by-products of the instant continuous process. Examples of other sulfate or sulfonate detergents are paraffin sulfonates, such as (1) the reaction products of alpha olefins and bisulfites (for example, sodium bisulfite), such as primary paraffin sulfonates of about 10 to 20, preferably about 15 to 20, carbon atoms and (2) paraffin sulfonates prepared by the sulfoxydation or sulfochlorination processes, which give a mixture of primary and secondary alkane sulfonates, predominantly secondary; sulfates of higher alcohols; salts of alpha-sulfofatty esters having about 10 to 20 carbon atoms, such as methyl alpha-sulfomyristate or alpha-sulfotallowate.

Examples of sulfates of higher alcohols are sodium lauryl sulfate, sodium tallow alcohol sulfate, Turkey Red Oil or other sulfated oils, or sulfates of mono- or diglycerides of fatty acids (for example, stearic monoglyceride monosulfate), alkyl poly-(ethenoxy) ether sulfates such as the sulfates of the condensation products of ethylene oxide and lauryl alcohol (usually having 1 to 5 ethenoxy groups per molecule); lauryl or other higher alkyl glyceryl ether sulfonates; aromatic poly(ethenoxy) ether sulfates such as the sulfates of the condensation products of ethylene oxide and nonyl phenol (usually having 1 to 6 oxyethylene groups per molecule).

The suitable anionic detergents include also the acyl sarcosinates (for example, sodium lauryoylsarcosinate), the acyl esters (for example, oleic acid ester) of isethionates, and the acyl N-methyl taurides (for example, potassium N-methyl lauroylor oleyl tauride).

The most highly preferred water-soluble anionic detergent compounds are the ammonium and substituted ammonium (such as mono-, di-, and triethanolamine), alkali metal (such as sodium and potassium) and alkaline earth metal (such as calcium and magnesium) salts of the higher alkyl benzene sulfonates, olefin sulfonates, the higher alkyl sulfates, and the higher fatty acid monoglyceride sulfates. The particular salt will be suitably selected depending upon the particular formulation and the proportions therein.

Nonionic surface active agents include those surface active or detergent compounds which contain an organic hydrophobic group and a hydrophillic group which is a reaction product of a solubilizing group such as carboxylate, hydroxyl, amido, or amino with ethylene oxide or with the polyhydration product thereof, polyethylene glycol.

As examples of nonionic surface active agents which may be used are the condensation products of alkyl phenols with ethylene oxide, for example, the reaction product of isooctyl phenol with about 6 to 30 ethylene oxide units; condensation products of alkyl thiophenols with 10 to 15 ethylene oxide units; condensation products of higher fatty alcohols such as tridecyl alcohol with ethylene oxide; ethylene oxide addends of monoesters of hexahydric alcohols and inner ethers thereof such as sorbitan monolaurate, sorbitol monooleate and mannitan monopalmitate, and the condensation products of polypropylene glycol with ethylene oxide.

Cationic surface active agents may also be employed. Such agents are those surface active detergent compounds which contain an organic hydrophobic group and a cationic solubilizing group. Typical cationic solubilizing groups are amine and quaternary groups.

Examples of suitable synthetic cationic detergents are the diamines such as those of the type $RNHC_2H_4NH_2$ wherein R is an alkyl group of about 12 to 22 carbon atoms, such as N-2-aminoethyl stearyl amine and N-2-aminoethyl myristyl amine; amide-linked amines such as those of the type $R^1CONHC_2H_4NH_2$ wherein $R^1$ is an alkyl group of about 9 to 20 carbon atoms, such as N-2-amino ethyl-stearyl amide and N-amino ethylmyristyl amide; quaternary ammonium compounds wherein typically one of the groups linked to the nitrogen atom is an alkyl group of about 12 to 18 carbon atoms and three of the groups linked to the nitrogen atom are alkyl groups which contain 1 to 3 carbon atoms, including such 1 to 3 carbon alkyl groups bearing inert substituents, such as phenyl groups, and there is present an anion such as halogen, acetate, methosulfate, etc. Typical quaternary ammonium detergents are ethyl-dimethyl-stearyl ammonium chloride, benzyl-dimethyl-stearyl ammonium chloride, trimethyl-stearyl ammonium chloride, trimethyl-cetyl ammonium bromide, dimethylethyl-dilauryl ammonium chloride, dimethyl-propyl-myristyl ammonium chloride, and the corresponding methosulfates and acetates.

Examples of suitable amphoteric detergents are those containing both an anionic and a cationic group and a hydrophobic organic group, which is advantageously a higher aliphatic radical, for example, having 10 to 20 carbon atoms. Among these are the N-long chain alkyl aminocarboxylic acids of the formula

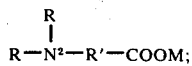

the N-long chain alkyl iminodicarboxylic acids of the formula RN(R'COOM)$_2$, and the N-long chain alkyl betaines of the formula

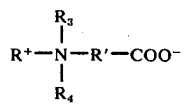

where R is a long chain alkyl group of about 10 to 20 carbons, R' is a divalent radical joining the amino and carboxyl portions of an amino acid (for example, an alkylene radical of 1 to 4 carbon atoms), M is hydrogen or a salt-forming metal, $R^2$ is a hydrogen or another monovalent substituent (for example, methyl or other lower alkyl group), and $R^3$ and $R^4$ are monovalent substituents joined to the nitrogen by carbon-to-nitrogen bonds (for example, methyl or other lower alkyl substituents). Examples of specific amphoteric detergents are N-alkyl-beta-aminopropionic acid; N-alkyl-beta-iminodipropionic acid, and N-alkyl, N,N-dimethyl glycine; the alkyl group may be, for example, that derived from coco fatty alcohol, lauryl alcohol, myristyl alcohol (or a lauryl-myristyl mixture), hydrogenated tallow alcohol, cetyl, stearyl, or blends of such alcohols. The substituted aminoproprionic and iminodipropionic acids are often supplied in the sodium or other salt form, which may likewise be used in the practice of this invention. Examples of other amphoteric detergents are the fatty imidazolines such as those made by reacting a long chain fatty acid of 10 to 20 carbon atoms with diethylene triamine and monohalocarboxylic acids having 2 to 6 carbon atoms, for example, 1-coco-5-hydroxyethyl-5-carboxymethylimidazoline; betaines containing a sulfonic group instead of the carboxylic group; betaines in which the long chain substituent is joined to the carboxylic group without an intervening nitrogen atom, for example, inner salts of 2-trimethylamino fatty acids such as 2-trimethylaminolauric acid, and compounds of any of the previously mentioned types but in which the nitrogen atom is replaced by phosphorus.

The relative proportions of the novel hydroxy ether sulfonate detergent to other detergents may vary widely within the range of 100:1 to 1:100, for example, 1:4, 1:2, 1:1, 2:1, or 4:1.

Water-soluble builder salts may also be present, in the usual proportions, in the detergent formulations when heavy duty cleaning is desired. These salts include phosphates and particularly condensed phosphates such as pyrophosphates or tripolyphosphates, silicates, borates, and carbonates (including bicarbonates), as well as organic builders such as salts of nitrilotriacetic acid or ethylene diamine tetracetic acid. Sodium and potassium salts are preferred. Specific examples are sodium tripolyphosphate, potassium pyrophosphate, sodium hexametaphosphate, sodium carbonate, sodium bicarbonate, sodium sesquicarbonate, sodium tetraborate, sodium silicate, salts (for example, Na salt) of methylene diphosphonic acid, trisodium nitrilotriacetate, or mixtures of such builders, including mixtures of pentasodium tripolyphosphate and trisodium nitrilotriacetate in a ratio, of these two builders, of 1:10 to 10:1, for example, 1:1. The proportions of builder salt may be, for example, 50 parts or more (for examples, 50 to 1000 parts) per 100 parts of detergent.

The detergent formulation may also contain other ingredients. Among these are soil-suspending agents such as sodium carboxymethyl cellulose or polyvinyl alcohol, preferably both, or other soluble polymeric materials, such as methyl cellulose, in the range of about 1/20 to 2 percent); antioxidants such as 2,6-ditertbutylphenol, or other phenolic antioxidant materials in amounts in the range of about 0.001 to 0.1 percent; coloring agents and optical brightening agents or fluorescent dyes in amounts in the range of about 1/20 to ½ percent. Among the optical brightening agents are such compounds as the fluorescent dyes of the stilbene type, such as sodium 2-sulfo-4-(2-naphtho-1,2 triazole) stilbene; disodium 4,4'-bis(4-anilino-6-morpholino-s-triazin-2-yl-amino) stilbenedisulfonate; or disodium 4,4'-bis(4,6-dianilino-s-triazin-2-yl-amino)-2,2'-stilbenedisulfonate; or of the oxazole type, for example, having a 1-phenyl 2-benzoxazole ethylene structure. For heavy duty built aqueous liquid formulations in particular (for example, liquids containing large amounts of dissolved tetrapotassium pyrophosphate), hydrotropic materials such as lower alkyl aryl sulfonates, for example, sodium toluene- or xylene sulfonate, can assist in processing and maintaining a compatible mixture; in general, these materials are present in minor amounts, usually in the range of about ½ to 15 percent (preferably 10 percent) of the total liquid composition.

Although, as previously indicated, the germicidal properties have been observed in the novel products of this invention, one may also add known germicidal ingredients to the detergent compositions. These include halogenated carbanilides, (such as trichlorocarbanilide), halogenated salicylanilide, (such as tribromosalicylanilide), halogenated bisphenols, (such as hexachlorophene), halogenated trifluoromethyl-diphenyl urea, zinc salt of 1-hydroxy-2-pyridinethione and the like. (These germicides are present in amounts in the range of about 1/50 to 2 percent).

Opacifiers, perfumes, and anti-tarnishing agents may also be included in the detergent compositions containing the novel hydroxy ether sulfonates as may oxygen- and chlorinereleasing bleaches, such as sodium perborate or sodium or potassium dichloroisocyanurate. Heavy-duty detergent compositions containing the new products may also contain sodium bromide in amount of 0.1 to 1 percent to improve the bleaching effect of the sodium hypochlorite present in the wash water.

The detergent compositions contaiing the novel hydroxy ether sulfonates may also contain enzymes to assist in the removal of stains. Particularly important among these are the proteolytic enzymes such as pepsin, trypsin, chymotrypsin, papain, bromelin, collagenase, keratinase, carboxylase, amino peptidase, elastase, subtilisia, and aspergillopepidase A and B. Among commercially available enzymes are Alcalase and Maxatase. The enzyme is preferably present in powdered form and is admixed into the detergent formulation, typically in an amount of about 0.001 to 4 percent of the total formulation, preferably about 0.05 to 1 percent. The combination of the novel hydroxy ether sulfonates with enzymes yields particularly efficacious results. The enzyme-containing product can be used in cool, tepid water, or hot water.

The manufacture of detergent products in bar form, such as toilet bars and laundry bars, from olefin sulfonate detergents is described in Belgian Pat. No. 698,280. The novel hydroxy ether sulfonate compounds can be substituted for the olefin sulfonates in the same proportions in each of the general and specific formulations set forth in that patent. The same or similar processing techniques may be used for blending the ingredients and for making the bars. For instance, the novel hydroxy ether sulfonates may be used as such, or with a plasticizer or with an equal weight of coconut oil/tallow soap, to make a toilet bar; or they may be mixed with an excess of pentasodium tripolyphosphate and 10-percent starch to make a built laundry detergent bar.

In the manufacture of oral preparations, the novel hydroxy ether sulfonates may be incorporated into toothpastes, dental creams, tooth powders, liquid dentifrices, mouth washes or rinses, dental chewing gums, lozenges, or troches. Thus, in a toothpaste the composition may comprise some 20 to 75 percent of dental polishing agent, together with water, a humectant such as glycerol, and a gelling agent such as sodium carboxymethyl cellulose. Fluorides such as stannous fluoride may be present. In general, the novel hydroxy ether sulfonate compounds of this invention may be substituted for the olefin sulfonates in each of the general and specific formulations set forth in the applications of Bouchal and Salzmann Ser. No. 579,497 filed Sept. 15, 1966, now U.S. Pat. No. 3,531,564, and of Rubinfeld and Levinsky Ser. No. 579,524, filed Sept. 15, 1966, now U.S. Pat. No. 3,462,525.

Shampoo formulations may comprise simple dispersions of the hydroxy ether sulfonate compounds in water, for example, in the form of alkanolammonium salts thereof, or combinations containing minor proportions of foam boosting agents such as fatty acid (for example, lauric-myristic) mono- or diethanolamides or the corresponding isopropanolamides or amine oxides such as lauryl dimethylamine oxide. Other surface active detergents such as soaps and sodium lauryl sulfate may also be present.

Specific examples of the formulation of these hydroxy ether sulfonates into various detergent compositions are found in U.S. Pat. application 736,753, now abandoned.

It is to be understood that the foregoing detailed description is merely given by way of illustration and that many variations may be made therein without departure from the spirit of the invention. The "Abstract" given above is merely for the convenience of searchers and is not to be given any weight in defining the scope of the invention.

We claim:

1. A continuous process for preparing gamma sultones which comprises the steps of (A) reacting from 1 to 1.5 moles of gaseous sulfur trioxide with a thin, flowing film of one mole of an olefin of 8 to 25 carbon atoms and an $\alpha$-olefin content above 70 percent by weight while maintaining the reaction temperature between 10° C. and 70° C. to form an acid mix containing gamma and delta sultones, alkene sulfonic acids, alkene disulfonic acids and virtually no olefin starting materials; (B) diluting the acid mix with an organic solvent selected from the group consisting of hydrocarbons having from 4 to 8 carbon atoms, halohydrocarbons having 1 to 8 carbon atoms and 1 to 8 halogen groups, lower alcohols having 1 to 4 carbon atoms and lower ketones having 3 to 4 carbon atoms to form a solvent-acid mix solution having a solvent-to-acid mix ratio between 1:1 and 5:1 at a temperature between 15° C. and 35° C.; (C) cooling the solvent-acid mix solution to a temperature below 10° C., thereby precipitating the gamma sultone from the acid mix as crystals; and (D) removing the gamma sultone crystals from said solvent-acid mix solution, said crystals being substantially free of contamination with other sulfonation reaction products.

2. A process in accordance with claim 1 wherein the solvent is a saturated hydrocarbon having a 4 to 8 carbon atom chain.

3. A process in accordance with claim 2 wherein said hydrocarbon is pentane or hexane.

4. A process in accordance with claim 1 wherein said solvent-acid mix solution is cooled to a temperature between 0° C. and 5° C.

5. A process in accordance with claim 1 wherein said gamma sultone crystals are removed by filtration.

6. A process in accordance with claim 5 which further includes the steps of passing the filtrate through a falling film evaporator to remove said solvent and neutralizing the solvent free acid mix with an alkali metal or ammonium hydroxide.

7. In a process for the preparation of gamma sultones which includes the steps of reacting at least one mole of gaseous sulfur trioxide with a falling film of one mole of an olefin of 8 to 25 carbon atoms having an $\alpha$ olefin content above 70 percent by weight at a temperature between about 10° C. and about 70° C. to form an acid mix containing gamma sultones and thereafter recovering said gamma sultones, the improvement wherein the gamma sultone is continuously removed directly from the acid mix by the steps of diluting the acid mix with an organic solvent selected from the group consisting of hydrocarbons having 4 to 8 carbon atoms, halohydrocarbons having 1 to 8 carbon atoms and 1 to 8 halogen groups, lower alcohols having 1 to 4 carbon atoms and lower ketones having 3 to 4 carbon atoms to form a solvent-acid mix solution having a solvent-to-acid mix ratio between 1:1 and 5:1 at temperature between 15° C. and 35° C., cooling the solvent-acid mix solution to below 10° C. whereby the gamma sultone precipitates as crystals, and removing the gamma sultone crystals from said solvent-acid mix solution.

* * * * *